US012590331B2

(12) United States Patent
Behar-Cohen et al.

(10) Patent No.: US 12,590,331 B2
(45) Date of Patent: Mar. 31, 2026

(54) METHODS OF DETERMINING WHETHER A SUBJECT HAS OR IS AT RISK OF HAVING A CENTRAL SEROUS CHORIORETINOPATHY

(71) Applicants: INSERM (Institut National de la Santé et de la Recherche Médicale), Paris (FR); Sorbonne Université, Paris (FR); Université Paris Cité, Paris (FR); Assistance Publique-Hôpitaux de Paris, Paris (FR); Fondation Asile des Aveugles, Lausanne (CH)

(72) Inventors: Francine Behar-Cohen, Paris (FR); Min Zhao, Paris (FR)

(73) Assignees: INSERM (INSTITUT NATIONAL DE LA SANTE ET DE LA RECHERCHE MEDICALE), Paris (FR); Sorbonne Université, Paris (FR); Université Paris Cité, Paris (FR); Assistance Publique-Hôpitaux de Paris (APHP), Paris (FR); Fondation Asile des Aveugles, Lausanne (CH)

( * ) Notice: Subject to any disclaimer, the term of this patent is extended or adjusted under 35 U.S.C. 154(b) by 748 days.

(21) Appl. No.: 17/905,899

(22) PCT Filed: Mar. 10, 2021

(86) PCT No.: PCT/EP2021/056109
§ 371 (c)(1),
(2) Date: Sep. 8, 2022

(87) PCT Pub. No.: WO2021/180818
PCT Pub. Date: Sep. 16, 2021

(65) Prior Publication Data
US 2023/0151425 A1 May 18, 2023

(30) Foreign Application Priority Data
Mar. 11, 2020 (EP) ..................................... 20305253

(51) Int. Cl.
*C12Q 1/68* (2018.01)
*A61K 31/585* (2006.01)
*C12P 19/34* (2006.01)
*C12Q 1/6883* (2018.01)

(52) U.S. Cl.
CPC .......... *C12Q 1/6883* (2013.01); *A61K 31/585* (2013.01); *C12Q 2600/106* (2013.01); *C12Q 2600/118* (2013.01); *C12Q 2600/158* (2013.01)

(58) Field of Classification Search
CPC ............................ C12Q 1/6883; A61K 31/585
See application file for complete search history.

(56) References Cited

PUBLICATIONS

Francine F Behar-Cohen, et al. "The multiple effects of mineralocorticoid antagonists for the treatment of retinal diseases" ARVO Annual Meeting Abstrac, Investigative Ophthalmology & Visual Science Jun. 2017, vol. 58, 4629. (Year: 2017).*
Sayan Ghosh, et al. "Activating the AKT2-nuclear factor-kB-lipocalin-2 axis elicits an inflammatory response in age-related macular degeneration" J Pathol 2017; 241: 583-588 (Year: 2017).*
Sayan Ghosh, et al. "The role of lipocalin-2 in age-related macular degeneration (AMD)" Cellular and Molecular Life Sciences (2020) 77:835-851. (Year: 2020).*
Juppner, H. "Functional Properties of the PTH/PTHrP Receptor" Bone vol. 17, No. 2, Supplement Aug. 1995:39S-42S (Year: 1995).*
Guoan Chen, et al "Discordant Protein and mRNA Expression in Lung Adenocarcinomas" Molecular & Cellular Proteomics 1:304-313, 2002 (Year: 2002).*
Vivian G. Cheung, et al. "Natural variation in human gene expression assessed in lymphoblastoid cells" Nature Genetics, vol. 33, Mar. 2003, pp. 422-425. (Year: 2003).*
J. Perren Cobb, et al. "Sepsis gene expression profiling: Murine splenic compared with hepatic responses determined by using complementary DNA microarrays" Crit Care Med 2002 vol. 30, No. 12, pp. 2711-2721. (Year: 2002).*
(Continued)

*Primary Examiner* — Stephen T Kapushoc
(74) *Attorney, Agent, or Firm* — WCF IP

(57) ABSTRACT

Central Serous chorioretinopathy (CSCR) is primarily an ocular disease, affecting the choroid and the retinal pigment epithelium. To date, no systemic biomarker of CSCR have been discovered that could link both forms and help the diagnosis in challenging cases. In the present invention, the inventors measure in European cohorts of CSCR patients (n=168) with (n=90) or without epitheliopathy (n=78) and a cohort of 153 control subjects without any ocular disease history, the serum levels of NGAL and the NGAL/MMP9 complex. Serum NGAL (ng/ml) was significantly higher in the control group (108.8±46.8) than in the CSCR cohort (80.4±46.4, p<0.0001). Serum NGAL (ng/ml) was significantly lower in the acute/recurrent cohort (n=78, 71.3±32.1) than in the control and, than in the chronic cohort (n=90, 88.3±55, p=0.03). Similarly, Serum NGAL/MMP9 (ng/ml) levels was lower in the whole CSCR cohort (44.5±39.6) as compared to the controls (77.6±47.8, p<0.0001). Serum NGAL/MMP9 (ng/ml) were significantly lower in the acute/recurrent cohort (37.6±37.9) than in the control and, than in the chronic cohort (50.5±40.3, p=0.002). Thus, in both forms of CSCR serum NGAL and NGAL/MMP9 are lower than in the control population, providing a biological link between the two forms and a potential susceptibility to oxidative stress and innate immune dysregulation. Systemic LCN2 being elevated in other retinal diseases, it represents a specific biomarker for CSCR.

7 Claims, 4 Drawing Sheets

(56) References Cited

PUBLICATIONS

Figure 1A:
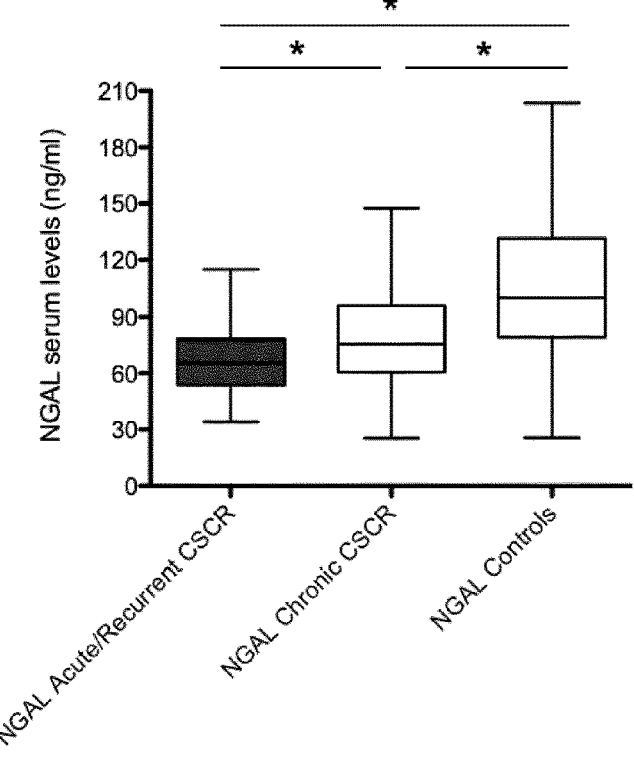

A. Matet; "Imaging and Biological Markers in Retinal Disorders to Assess Gene Therapy Safety and Investigate Vascular Disease Mechanisms"; PhD Dissertation, University of Lausanne, Jan. 1, 2017, entire document.

\* cited by examiner

ROC curve NGAL serum levels in acute/recurrent CSCR versus controls

ROC curve NGAL/MMP9 serum levels in acute/recurrent CSCR versus controls

NGAL serum levels

METHODS OF DETERMINING WHETHER A SUBJECT HAS OR IS AT RISK OF HAVING A CENTRAL SEROUS CHORIORETINOPATHY

FIELD OF THE INVENTION

The present invention is in the field of medicine, in particular ophthalmology.

BACKGROUND OF THE INVENTION

Central Serous chorioretinopathy is primarily an ocular disease, affecting the choroid and the retinal pigment epithelium (RPE)[1]. Different forms of the disease are recognized although a consensus nomenclature is still missing[2]. Most of patients present with a focal RPE leakage site that causes a spontaneously resolving and sometimes recurrent serous detachment, whilst a minority of patients presents with widespread pigment epitheliopathy, persistent serous detachment and potential functional and anatomical complications[1]. The exact mechanisms and the causative factors for the disease remain uncertain. The more widely recognized risk factors for CSCR are: exposure to exogenous or endogenous corticoids, psychopharmacologic medication use and type A behavior, cardiovascular risk factors such as coronaropathy and hypertension, sleep disorders and shift work, and *Helicobacter pylori* infection[3]. Genetic predisposing factors have been identified, such as polymorphism in genes encoding complement factor system regulators[4], haplotype in the gene encoding the mineralocorticoid receptor[5], polymorphism in genes encoding plasminogen activator system[6] and VIP receptor[7]. Although, diagnosis is easily made based on the clinical presentation and imaging technologies such as SD-OCT and fluorescein and ICG angiography for typical presentations, it can be challenging in more complex cases, particularly in women, when choroid is thin and/or there are no favoring factors. To our knowledge, no systemic biomarker of CSCR has been identified.

Lipocalin-2 (LCN2), which human ortholog is Neutrophil Gelatinase-Associated Lipocalin, NGAL, alias siderocalin, uterocalin or 24p3, is a 21KD molecule that belongs to the lipocalins superfamily. Lipocalins transport small hydrophobic substances such as retinoids, steroids or fatty acids. In addition, LCN2 transports iron into cells and acts as an important regulator of the innate immunity, partly through its iron-regulating effects[8,9]. LCN2 is expressed in number of cells and tissues, such as innate immune cells, epithelial cells, brain astrocytes and, in retinal pigment epithelial cells[10] and retinal glial Müller cells[11]. LCN2 is induced in response to acute injury, infection and metabolic disturbance by NF-κB activation[12,13]. But, depending on the kinetic of disease (acute vs chronic) and on the organ, LCN2 exerts pro or anti-inflammatory actions. LCN2 favored inflammation in metabolic inflammation such as type 2 diabetes or in non-alcoholic via recruitment of neutrophils and proinflammatory cytokines[14]. In transgenic mice in which lysosome-mediated clearance in RPE cells is defective causing phenotypic features of early AMD in the mouse retina, LCN2 produced by neutrophils was shown to enhance their retinal infiltration contributing to age-related changes[15]. On the other hand, LCN2 showed anti-inflammatory effects in gut inflammation and, in LPS-induced inflammation in the brain[16] and in the eye, through the inactivation of NF-κB[11]. Another function of LCN2 is to promote MMP-9 activity by forming a complex with the protease (MMP-9/NGAL)[17], an important mediator of atheroma plaque instability. In experimental model of atherosclerosis, LCN2 plays a dual role, protecting from the early formation of plaques but enhancing MMP-9 activity and necrotic core size in advanced atherosclerosis[18].

In the retina, the role of LCN2 is incompletely understood. It is the most early-stress gene expressed in RPE and in the neural retina after exposing to light Abca4-/-Rdh8-/- mice, a model of AMD. LCN2 is protecting in this model since gliosis and microglial activation were enhanced in triple Lcn2-/- Abca4-/-Rdh8-/- mice submitted to light exposure[10,19]. In addition, LCN2 protected against oxidative stress by increasing the expression of the antioxidant enzymes HMOX1 and SOD2 in hiPS-RPE cells[19]. On the other hand, in another study, LCN2 facilitated light-induced photoreceptors apoptosis by increasing reactive oxygen species generation and Bim expression[20].

LCN2 has been identified as a biomarker for inflammatory and metabolic diseases[21] and is recognized as one of the best marker for diagnostic and prognostic of acute kidney injury[22, 23, 24, 25]. In kidney diseases, LCN2 is not only a biomarker of disease but contributes in pathogenic mechanisms[26]. LCN2 is also a biomarker of atherosclerosis, myocardial infarction (MI) and heart failure[27]. After MI, LCN2 produced by neutrophils induces the polarization of macrophages towards a phenotype that allows clearance of apoptotic cells and reduces cardiac fibrosis. LCN2 is thus beneficial for cardiac remodeling[28].

In ocular diseases, increased LCN2 levels were measured in the aqueous humors but not in the serum of patients with central retinal vein occlusion.[29] In patients with diabetic retinopathy, plasma LCN2 levels were elevated and correlated with the severity of retinopathy[30]. In AMD, plasma LCN2 levels were elevated and LCN2 was increased in aqueous humor of patients with wet AMD[31].

SUMMARY OF THE INVENTION

The present invention is defined by the claims. In particular, the present invention relates to methods of determining whether a subject has or is at risk of a central serous chorioretinopathy.

DETAILED DESCRIPTION OF THE INVENTION

Two major forms Central Serous chorioretinopathy (CSCR) are recognized depending on whether there is an associated clinically detected epitheliopathy that defines the chronic forms.

Whether chronic CSCR results only from the evolution of acute form or is an independent entity remains uncertain. To date, no systemic biomarker of CSCR have been discovered that could link both forms and help the diagnosis in challenging cases.

Lipocalin 2 (Lcn2, Neutrophil gelatinase associated lipocalin, NGAL), a 25 kD secreted protein has multiple innate immune functions. NGAL also exist as a disulphide-linked heterodimer bound to MMP9, that stabilizes MMP9 activity. Systemic LCN2 is increased in diabetic retinopathy, age-related macular degeneration and retinitis pigmentosa.

To measure in European cohorts of CSCR patients (n=168) with (n=90) or without epitheliopathy (n=78) and a cohort of 153 control subjects without any ocular disease history, the serum levels of NGAL and the NGAL/MMP9 complex. Subjects with CRP>5 mg/L, creatinine >100 μmol/ L, urea >7.5 mmol/L were excluded.

Mean age in the control group was significantly younger than in the CSCR group and there was significantly more female in the control group than in the CSCR cohort but there was no significant correlation between NGAL or NGAL/MMP9 and the age or the sex. Serum NGAL (ng/ml) was significantly higher in the control group (108.8±46.8) than in the CSCR cohort (80.4±46.4, p<0.0001). Serum NGAL (ng/ml) was significantly lower in the acute/recurrent cohort (n=78, 71.3±32.1) than in the control and, than in the chronic cohort (n=90, 88.3±55, p=0.03). Similarly, Serum NGAL/MMP9 (ng/ml) levels was lower in the whole CSCR cohort (44.5±39.6) as compared to the controls (77.6±47.8, p<0.0001). Serum NGAL/MMP9 (ng/ml) were significantly lower in the acute/recurrent cohort (37.6±37.9) than in the control and, than in the chronic cohort (50.5±40.3, p=0.002). ROC curve showed that for serum levels of NGAL, a cutoff value of 80 ng/mL allows to discriminate acute/recurrent CSCR from controls with 79.5% sensitivity and 74.8% specificity and for serum levels of the NGAL/MMP9 complex, a cutoff value of 40 ng/mL allows to discriminate acute/recurrent CSCR from controls with 72.7% sensitivity and 76.0% specificity.

Thus, in both forms of CSCR serum NGAL and NGAL/1VMP9 are lower than in the control population, providing a biological link between the two forms and a potential susceptibility to oxidative stress and innate immune dysregulation. Systemic LCN2 being elevated in other retinal diseases, it represents specific biomarker for CSCR.

Accordingly, the first object of the present invention relates to a method of determining whether a subject has or is at risk of having a central serous chorioretinopathy comprising determining the level of NGAL in a sample obtained from the subject wherein said level indicates whether the subject has or is at risk of having a central serous chorioretinopathy.

As used herein, the term "central serous chorioretinopathy" or "CSCR" has its general meaning in the art and refers to a disorder characterized by serous retinal detachment and/or retinal pigment epithelial (RPE) detachment, changes most often confined to the macula, and associated with leakage of fluid through the RPE into the subretinal space. CSCR is seen frequently in most retina practices, classically in young male patients with no associated systemic conditions.

As used herein, the term "risk" in the context of the present invention, relates to the probability that an event will occur over a specific time period and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no-conversion. "Risk evaluation," or "evaluation of risk" in the context of the present invention encompasses making a prediction of the probability, odds, or likelihood that an event or disease state may occur, the rate of occurrence of the event or conversion from one disease state to another. Risk evaluation can also comprise prediction of future clinical parameters, traditional laboratory risk factor values, or other indices of relapse, either in absolute or relative terms in reference to a previously measured population. The methods of the present invention may be used to make continuous or categorical measurements of the risk of conversion, thus diagnosing and defining the risk spectrum of a category of subjects defined as being at risk of conversion. In the categorical scenario, the invention can be used to discriminate between normal and other subject cohorts at higher risk. In some embodiments, the present invention may be used so as to discriminate those at risk from normal.

In some embodiments, the method described herein is applied to a subject who presents symptoms of CSCR without having undergone the routine screening to rule out all possible causes for CSCR. The methods described herein can be part of the routine set of tests performed on a subject who presents symptoms of CSCR such as blurry vision, distortion, blind spots, muted colours, objects appearing smaller than they are, trouble with bright light and/or reduced ability to see an object against a background of similar colour (contrast sensitivity). The method of the present invention can be carried out in addition of other diagnostic tools that include blue fundus autofluorescence imaging, spectral-domain optical coherence tomography and/or fluorescein angiography.

In some embodiments, the sample is a blood sample. As used herein the term "blood sample" means any blood sample derived from the subject. Collections of blood samples can be performed by methods well known to those skilled in the art. In some embodiments, the blood sample is a serum sample or a plasma sample.

As used herein, the terms "Lipocalin 2", "Lcn2" or "NGAL" have their general meaning in the art and refer to the Neutrophil Gelatinase-Associated Lipocalin as described in Schmidt-Ott K M. et al. (2007). NGAL can be from any source, but typically is a mammalian (e.g., human and non-human primate) NGAL, particularly a human NGAL. An exemplary human native NGAL amino acid sequence is provided in GenPept database under accession number NP 005555. NGAL is a glycoprotein and was originally identified as a neutrophil specific granule component and a member of the lipocalin family of proteins. The protein was shown to exist both as a 25-kDa monomer and a 45-kDa disulfide-linked homodimer, and it may also be covalently complexed with neutrophil gelatinase (also known as matrix metalloproteinase 9, MMP-9) via an intermolecular disulphide bridge as a 135-kDa heterodimeric form.

Methods for determining the expression level of NGAL are well known in the art. For instance any conventional methods for determining the level of a protein in a sample can be used. In some embodiments, the methods of the invention comprise contacting the sample with a binding partner capable of selectively interacting with the protein liable to be present in the sample. The binding partner may be an antibody that may be polyclonal or monoclonal, preferably monoclonal. In some embodiments, the binding partner may be an aptamer. The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal. As used herein, the term "labelled", with regard to the antibody, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. The afore mentioned assays generally involve the binding of the binding partner (ie. antibody or aptamer) to a solid support. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like. The level of biomarker protein may be measured by using standard immuno diagnostic techniques, including immunoassays such as competition, direct reaction, or sandwich type assays. Such assays include, but are not limited to, agglutination tests; enzyme-labelled and mediated immunoassays, such as ELISAs; biotin/avidin type assays; radioimmunoassays; Immunoelectrophoresis; immunoprecipitation. More particularly, an ELISA method can be used, wherein e.g. the wells of a microtiter plate are coated with a set of antibodies which recognize said biomarker protein. The sample containing or suspected of containing said biomarker protein is then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art. In some embodiments, the immunoassay may involve the use of 2 antibodies having specificity for the protein. Typically, a first antibody is used as to "detect" the protein and the second antibody is used to "capture" the protein. In some embodiments, the method is achieved by i) providing a solid support coating with an amount of first antibodies specific for the protein, ii) bringing the sample into contact with the solid support, iii) and adding an amount of the second antibodies conjugated to a label. Measuring the amount of bound binding partner which is specific for the label reveals the amount of the protein present in the sample. Typically, the first antibody is directed to an epitope which does not prevent the interaction with the second antibody. Typically washing steps (with any appropriate buffer such as PBS with or without a non-ionic detergent) are performed after steps ii) and iii). Typically, a blocking step is performed with a buffer containing BSA or milk and/or serum (goat or bovine) to block non-specific binding of the proteins. Measuring the level of the biomarker protein (with or without immunoassay-based methods) may also include separation of the compounds: centrifugation based on the compound's molecular weight; electrophoresis based on mass and charge; HPLC based on hydrophobicity; size exclusion chromatography based on size; and solid-phase affinity based on the compound's affinity for the particular solid-phase that is used. Once separated, said biomarker protein may be identified based on the known "separation profile" e. g., retention time, for that compound and measured using standard techniques. Alternatively, NGAL may be detected and measured by, for example, a mass spectrometer.

In some embodiments, the level of NGAL is compared to a predetermined reference value. The predetermined reference value is typically a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement in properly banked historical subject samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the level of NGAL, one can use algorithmic analysis for the statistic treatment of the levels determined in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is high. This algorithmic method is preferably done with a computer. Existing software or systems in the art may be used for the drawing of the ROC curve, such as: MedCalc 9.2.0.1 medical statistical software, SPSS 9.0, ROCPOW-ER.SAS, DESIGNROC.FOR, MULTIREADER POWER. SAS, CREATE-ROC. SAS, GB STAT VI0.0 (Dynamic Microsystems, Inc. Silver Spring, Md., USA), etc.

In some embodiments, the predetermined reference value is the level of NGAL determined in a population of healthy individuals. Typically, it is concluded that the patient suffers from CSCR or is at risk of relapse when the level of NGAL is lower (at least 0.5, 1, 1.5, 2, 2.5, 3, 3.5, 4, 5, 6, 7, 8, 9, 10, 15, 20, 30, 40, 50, 100 fold lower) than the level determined in a population of healthy individuals.

The method of the present invention is particularly suitable for the differential diagnosis between CSCR and other ocular diseases such as Age-related Macular Degeneration (AMD) in which the level of NGAL is typically higher than the predetermined reference value. Thus a further object of the present invention relates to a method for the differential diagnosis between CSCR and AMD in a subject comprising determining the level of NGAL in a sample obtained from the subject wherein high level of NGAL indicates that the subject suffers from AMD and low level of NGAL indicates that the subject suffers from CSCR.

As used herein, the term "high" refers to a measure that is greater than normal, greater than a standard such as a predetermined reference value or a subgroup measure or that is relatively greater than another subgroup measure. For example, a high expression level refers to a level of NGAL that is greater than a normal level of NGAL in a particular set of samples of patients. A normal level of NGAL may be determined according to any method available to one skilled in the art. High level of NGAL may also refer to a level that is equal to or greater than a predetermined reference value, such as a predetermined cutoff. High level of NGAL may also refer to a level of NGAL wherein a high level subgroup has relatively greater level of NGAL than another subgroup. For example, without limitation, according to the present specification, two distinct patient subgroups can be created by dividing samples around a mathematically determined point, such as, without limitation, a median, thus creating a subgroup whose measure is high (i.e., higher than the median) and another subgroup whose measure is low. In some cases, a "high" level may comprise a range of level that is very high and a range of level that is "moderately high" where moderately high is a level that is greater than normal, but less than "very high".

As used herein, the term "low" refers to a level of NGAL that is less than normal, less than a standard such as a predetermined reference value or a subgroup measure that is relatively less than another subgroup level. For example, low level of NGAL means a level of NGAL that is less than a normal level of NGAL in a particular set of samples of patients. A normal level of NGAL may be determined according to any method available to one skilled in the art. Low level of NGAL may also mean a level that is less than a predetermined reference value, such as a predetermined cutoff. Low level of NGAL may also mean a level wherein a low level subgroup is relatively lower than another subgroup. For example, without limitation, according to the present specification, two distinct patient subgroups can be created by dividing samples around a mathematically determined point, such as, without limitation, a median, thus creating a group whose measure is low (i.e., less than the median) with respect to another group whose measure is high (i.e., greater than the median). In some cases, a "low" level may comprise a range of level that is very low and a range of level that is "moderately low" where moderately low is a level that is lower than normal, but higher than "very low".

A further object of the present invention relates to a method of predicting the risk of relapse in a subject suffering from CSCR comprising determining the level of NGAL in a sample obtained from the subject wherein said levels indicates the risk of relapse.

As used herein, the term "relapse" refers to the return of signs and symptoms of a disease after a subject has enjoyed a remission after a treatment. Thus, if initially the target disease is alleviated or healed, or progression of the disease was halted or slowed down, and subsequently the disease or one or more characteristics of the disease resume, the subject is referred to as being "relapsed".

A further object of the present invention relates to a method of determining whether the subject suffering from CSCR achieves a response with a treatment comprising i) determining the level of NGAL in a sample obtained from the subject before the treatment ii) determining the level of NGAL in a sample obtained from the subject before the treatment, iii) comparing the level determined at step i) with the level determined at step ii) and iv) concluding that the subject achieves a response when the level determined at step ii) is higher than the level determined at step i).

The method is thus particularly suitable for discriminating responder from non-responder. As used herein the term "responder" in the context of the present disclosure refers to a subject that will achieve a response, i.e. a subject who is under remission and more particularly a subject who does no longer suffer from CSCR. A non-responder subject includes subjects for whom the disease does not show reduction or improvement after the treatment.

According to the present invention, the treatment consists in any method or drug or therapy that could be suitable for the treatment of CSCR. For instance, the drug or therapy consists of anti-VEGF agents, Carbonic Anhydrase Inhibitors, Mineralocorticoid Antagonists, Laser Photocoagulation, Diode Micropulse Laser, Verteporfin photodynamic therapy (PDT) and/or Transpupillary Thermotherapy.

As used herein an "anti-VEGF agent" refers to a molecule that inhibits VEGF-mediated angiogenesis. For example, an anti-VEGF therapeutic may be an antibody to or other antagonist of VEGF. An "anti-VEGF antibody" is an antibody that binds to VEGF with sufficient affinity and specificity to be useful in a method of the invention. An anti-VEGF antibody will usually not bind to other VEGF homologues such as VEGF-B or VEGF-C, or other growth factors such as P1GF, PDGF or bFGF. A preferred anti-VEGF antibody is a monoclonal antibody that binds to the same epitope as the monoclonal anti-VEGF antibody A4.6.1 produced by hybridoma ATCC® HB 10709 and is a high-affinity anti-VEGF antibody. A "high-affinity anti-VEGF antibody" has at least 10-fold better affinity for VEGF than the monoclonal anti-VEGF antibody A4.6.1. Preferably the anti-VEGF antibody is a recombinant humanized anti-VEGF monoclonal antibody fragment generated according to WO 98/45331, including an antibody comprising the CDRs or the variable regions of Y0317. More preferably, anti-VEGF antibody is the antibody fragment known as ranibizumab (LUCENTIS®). The anti-VEGF antibody ranibizumab is a humanized, affinity-matured anti-human VEGF Fab fragment. Ranibizumab is produced by standard recombinant technology methods in *E. coli* expression vector and bacterial fermentation. Ranibizumab is not glycosylated and has a molecular mass of –48,000 daltons. See WO98/45331 and U.S. 2003/0190317. Anti-VEGF agents include but are not limited to bevacizumab (rhuMab VEGF, Avastin®, Genentech, South San Francisco Calif.), ranibizumab (rhuFAb V2, Lucentis®, Genentech), pegaptanib (Macugen®, Eyetech Pharmaceuticals, New York N.Y.), sunitinib maleate (Sutent®, Pfizer, Groton Conn.). In some embodiments, the anti-VEGF agent is a dimeric fusion protein capable of binding VEGF with a high affinity composed of two receptor-Fc fusion protein consisting of the, principal ligand-binding portions of the human VEGFR1 or VEGFR2 receptor extracellular domains fused to the Fc portion of human IgGI (termed a "VEGF trap"). Specifically, the VEGF trap consists of Ig domain 2 from VEGFR1, which is fused to Ig domain 3 from VEGFR2, which in turn is fused to the Fc domain of IgGI.

As used herein the term "MR antagonist" has its general meaning in the art. The MR antagonistic of a compound may be determined using various methods as described in J, Souque A, Wurtz J M, Moras D, Rafestin-Oblin M E. Mol Endocrinol. 2000 August; 14(8):1210-21; Fagart J, Seguin C, Pinon G M, Rafestin-Oblin M E. Mol Pharmacol. 2005 May; 67(5):1714-22 or Hellal-Levy C, Fagart J, Souque A, Wurtz J M, Moras D, Rafestin-Oblin M E. Mol Endocrinol. 2000 August; 14(8):1210-21. For example, the mineralocorticoid receptor antagonists according to the invention generally are spirolactone-type steroidal compounds. The term "spironolactone-type" is intended to characterize a structure comprising a lactone moiety attached to a steroid nucleus, typically at the steroid "D" ring, through a spiro bond configuration. A subclass of spironolactone-type mineralocorticoid receptor antagonist compounds consists of epoxy-steroidal mineralocorticoid receptor antagonist compounds such as eplerenone. Another subclass of spironolactone-type antagonist compounds consists of non-epoxy-steroidal mineralocorticoid receptor antagonist compounds such as spironolactone. Mineralocorticoid receptor antagonists according to the invention may also be non-steroidal. For example, classes of non-steroidal MR antagonists have just begun to emerge over the past few years (Meyers, Marvin J1; Hu, Xiao Expert Opinion on Therapeutic Patents, Volume 17, Number 1, January 2007, pp. 17-23(7) and Piotrowski D W. Mineralocorticoid Receptor Antagonists for the Treatment of Hypertension and Diabetic NephropathyJ. Med. Chem. 2012, 55, 7957-7966). For instance, dihydropyrymidines have been shown to display MR antagonism (Activation of Mineralocorticoid Receptors by Exogenous Glucocorticoids and the Development of Cardiovascular Inflammatory Responses in Adrenalectomized Rats. Young M J, Morgan J, Brolin K, Fuller P J, Funder J W. Endocrinology. 2010 Apr. 21). Furthermore, Arhancet el al. disclose other class of non-steroidal MR antagonists (Arhancet G B, Woodard S S, Dietz J D, Garland D J, Wagner G M, Iyanar K, Collins J T, Blinn J R, Numann R E, Hu X, Huang H C. Stereochemical Requirements for the Mineralocorticoid Receptor Antagonist Activity of Dihydropyridines. J Med Chem. 2010 Apr. 21). Other exemplary non-steroidal mineralocorticoid receptor antagonists include but are not limited to those described in US 20090163472 WO2004052847, WO 2008053300 WO2008104306, WO2007025604, WO201264631, WO2008126831, WO2012008435, WO2010104721, WO200985584, WO200978934, WO2008118319, WO200917190, WO200789034, WO2012022121, WO2012022120, WO2011141848 and WO200777961 that are hereby incorporated by reference into the present disclosure.

A further object of the present invention relates to a method of treating CSCR in a subject in need thereof comprising i) determining whether the subject has or is at risk of having CSCR according to the method of the present invention and ii) and administering to the therapy or the drug as above described when it is considered that the subject has or is at risk of having CSCR.

The invention will be further illustrated by the following figures and examples. However, these examples and figures should not be interpreted in any way as limiting the scope of the present invention.

FIGURES

FIG. 1A: NGAL serum levels (ng/ml) in patients with acute/recurrent and in patients with chronic CSCR as compared to controls.

Figure 1B:
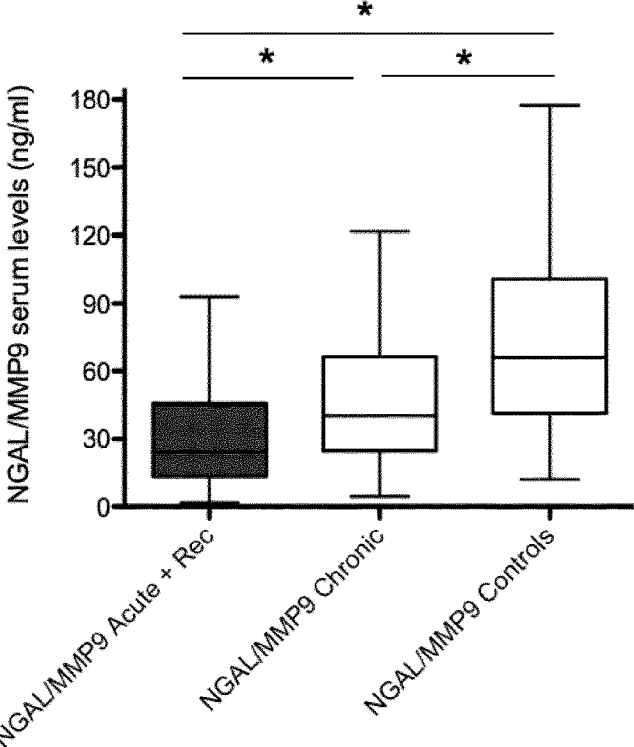

FIG. 1B: NGAL/MMP9 serum levels (ng/ml) in patients with acute/recurrent and in patients with chronic CSCR as compared to controls.

Figure 2:
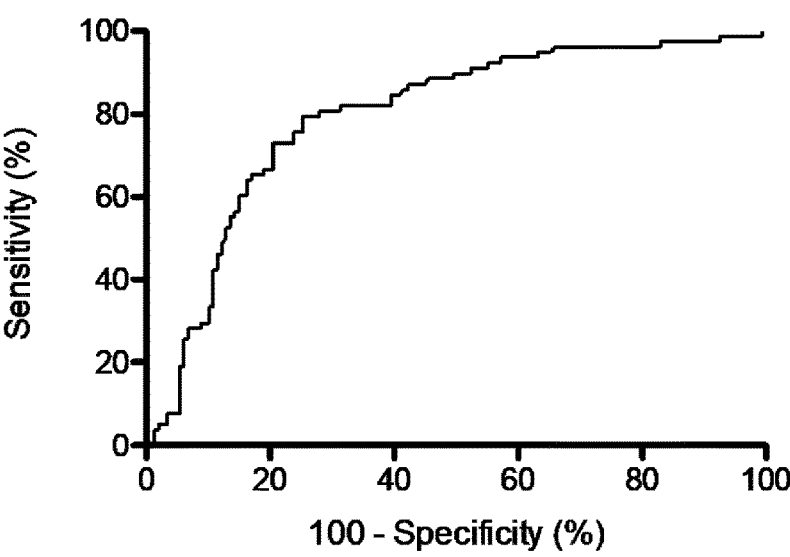

FIG. 2: ROC curve NGAL serum levels in acute/recurrent CSCR vs control FIG. 3: ROC curve NGAL/MMP9 serum levels in acute/recurrent CSCR vs control.

Figure 4:
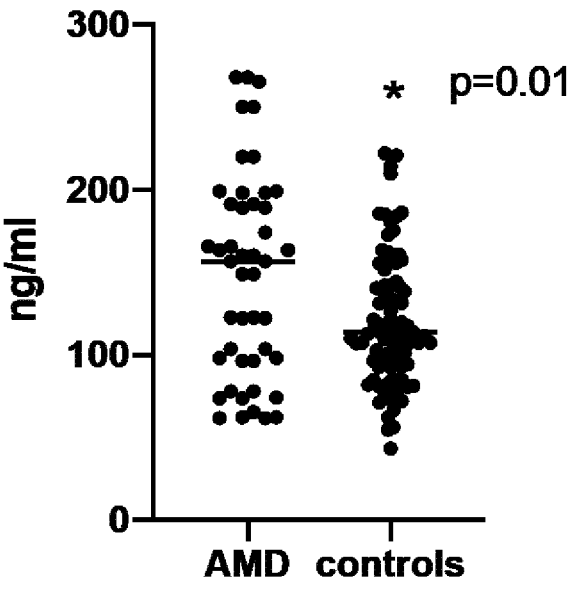

FIG. 4: NGAL serum levels (ng/ml) in patients with wet AMD as compared to controls.

Figure 5:
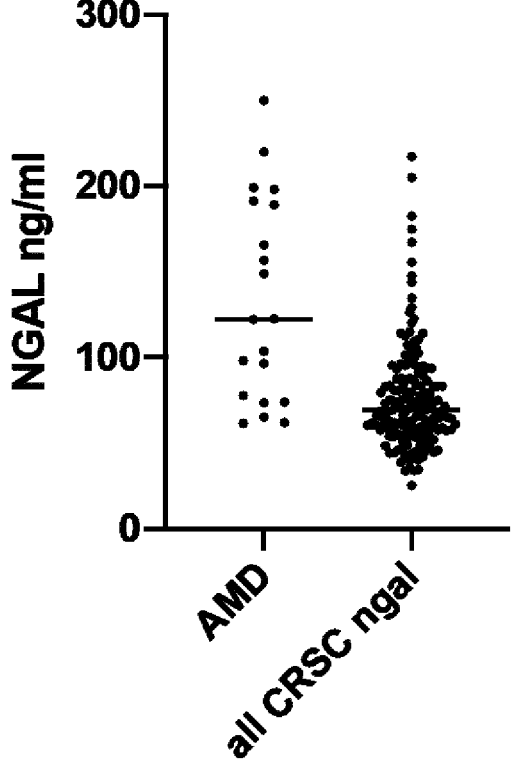

FIG. 5: NGAL serum levels (ng/ml) in patients with wet AMD as compared to patients with CSCR.

Figure 6:
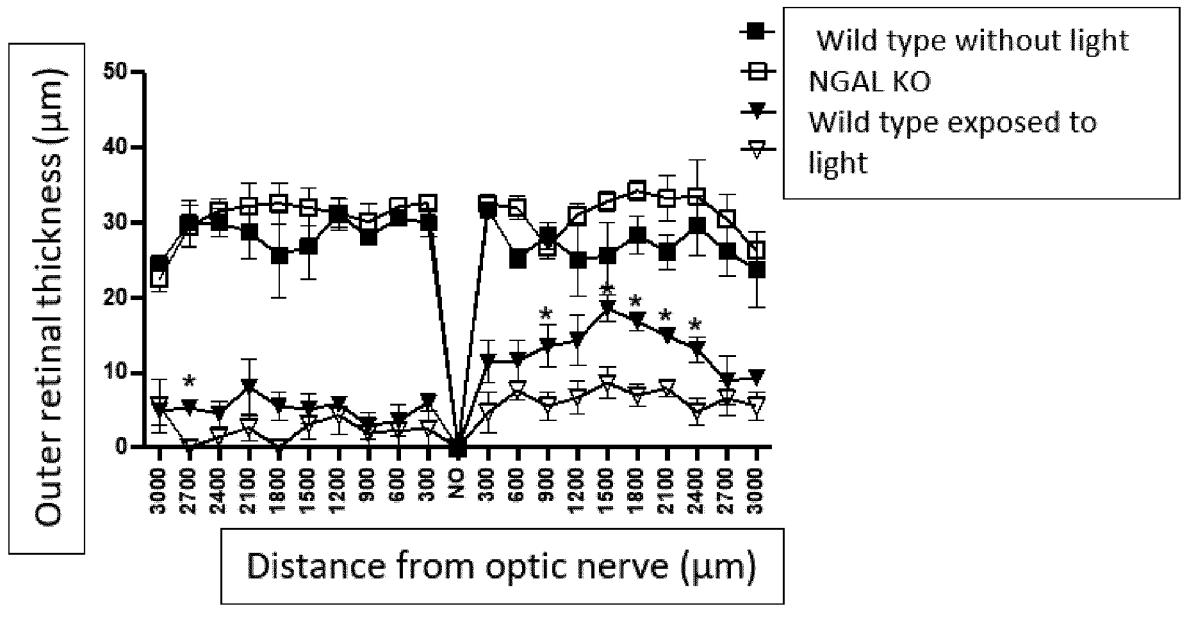

FIG. 6: Outer retinal thickness ($\mu$m) in function of distance from optic nerve ($\mu$m) in mice.

EXAMPLE

Methods

Patients:

Patients from 3 cohorts recruited at the Jules Gonin Eye Hospital (Lausanne, Switzerland), the Ophthalmopole Cochin hospital (Paris, France) and the Rotterdam Eye Hospital (Rotterdam, Netherland) were included. Serum analysis had been planned in Paris before the samples were collected in the different centers. The cases selection was based on the availability of samples from patients with well-defined phenotypes on multimodal retinal imaging.

Diagnosis criteria for CSCR were defined on multimodal imaging including blue fundus autofluorescence imaging, spectral-domain optical coherence tomography (SD-OCT, Spectralis, Heidelberg Engineering, Heidelberg, Germany) and fluorescein angiography. Patients were divided in two groups based on the presence of an underlying multifocal epitheliopathy characterized on blue autofluorescence and on fluorescein angiography. Patients with epitheliopathy were classified as chronic cases, while patients without epitheliopathy were classified as acute/recurrent cases.

Patients with any other ocular disease such as age-related macular degeneration (characterized by the presence of drusens), diabetic retinopathy, retinal vein occlusion, high myopia >−6D, or glaucoma were excluded from the study.

Serum from control subjects were obtained from the Banque Francaise du Sang (BFS) under an agreement between BFS and Inserm. Blood was collected from donors who had no previous history of ocular diseases.

Ethics Statement

This research was conducted in compliance with the tenets of the Declaration of Helsinki and was approved by our institutional review board of each country with authorization of IRB in France (CPP Ile de France 1, C16-09 N° DC-2016-2620, in Switzerland (CER-VD Eyeomics340/15) and in the Netherlands. Written informed consent was obtained for each patient and healthy participant.

LCN2 and NGAL/MMP9 Serum Levels Measurements

Human Lipocalin-2/NGAL Quantikine ELISA Kit and Human MMP-9/NGAL Complex Quantikine ELISA Kit (R &D Systems®, catalog number DLCN20 and DM9L20 respectively, Minneapolis, MN) were used to measure NGAL and NGAL/MMP9 complex according to the manufacturer protocol. All samples were tested in duplicated and required a 20-Fold dilution. Because LCN2 levels are influenced by kidney function[26] and by inflammatory state[21], patients with CRP>5 mg/L, creatinine >100 $\mu$mol/L, urea >7.5 mmol/L were excluded (53 and 24 subjects were excluded in the CSCR and control groups respectively). Elisa analysis was performed in Paris in 2019 by JC and TJ blind to diagnoses.

Statistics

Descriptive, comparative and correlative statistics were computed on GraphPad Prism (version 5.0f, GraphPad Software). Quantitative values were expressed as mean±standard deviation. The Kolmogorov-Smirnov test was employed to assess the normal or non-normal distribution of quantitative values. The Mann-Whitney test was employed to compare quantitative values, and the Spearman correlation coefficient was computed to assess correlations. The Fisher's exact test or the Chi-square test were employed to compare proportions between subgroups, where appropriate. Receiver operating characteristics (ROC) curves were plotted and analyzed to assess the sensitivity, specificity, and cutoff values of serum marker levels. P values inferior to 0.05 were considered significant.

Results

Demographic Characteristics of the Cohort

The demographic characteristics of 168 patients with CSCR and the 153 controls are shown in Table 1. Mean age in the control group was significantly younger (43±12.8 years) than in the CSCR group (50.1±10.7, p=0.0002). The mean age of chronic CSCR patients (n=90, 55.2±9.9) was also higher than the one of acute/recurrent cases (n=78 44.1±8.2, p<0.0001). But there was no significant difference in the age of patients with acute/recurrent CSCR as compared to the control group (p=0.83). There was significantly more female in the control group than in the CSCR cohorts, but the difference was not significant in the chronic CSCR as compared to control since there was more women affected in the chronic form than in the acute form.

Serum Levels of NGAL/LCN2 and NGAL (LCN2)/MMP9 are Lower in CSCR than in Control Subjects Serum levels of NGAL (LCN2) and the LCN2/MMP9 (NGAL/MMP9) complex in 168 patients with CSCR and 153 controls are shown in Table 2 and in FIG. 1A. Serum NGAL (ng/ml) was significantly higher in the control groups (108.8±46.8) than in the CSCR cohort (80.4±46.4, p<0.0001). Serum NGAL (ng/ml) was significantly lower in the acute/recurrent cohort (n=78, 71.3±32.1) than in the control and, than in the chronic cohort (n=90, 88.3±55, p=0.03). Similarly, Serum NGAL/MMP9 (ng/ml) levels was lower in the whole CSCR cohort (44.5±39.6) as compared to the controls (77.6±47.8, p<0.0001). Serum NGAL/MMP9 (ng/ml) were significantly lower in the acute/recurrent cohort (n=78, 37.6±37.9) than in the control and, than in the chronic cohort (n=90, 50.5±40.3, p=0.002), Table 2 and FIG. 1B.

Serum Levels of NGAL/LCN2 and NGAL (LCN2)/MMP9 are Lower in Male CSCR than in Male Control Subjects Since there was a significant difference in the sex ratio of the control cohort and the CSCR cohort, we also evaluated the serum levels of lipocalin (NGAL) and the lipocalin/MMP9 complex (NGAL/MMP9) in 141 male patients with CSCR and 112 male controls (Table 3) to eliminate a possible sex-induced confounding factor. In the male population, like in the whole cohorts, the levels of LCN2 (NGAL, ng/ml) were lower in the CSCR patients than in the controls (80.7±47.7 vs 101.5±41.7, p<0.001) and levels were lower in the acute/recurrent forms as compared to the chronic forms (71.9±33.1 vs 89.1±57.5, p=0.004). NGAL/MMP9 levels (ng/ml) were also lower in the CSCR cohort than in the control male cohort 43.1±37.7 vs72.2±42.7, p<0.0001) and lower in the acute/recurrent forms than in the chronic ones (36.8±38.5 vs 49.1±36.4, p=0.001).

Serum Levels of NGAL/LCN2 and of NGAL/MMP9 do not Correlate with Age in the CSCR and in the Control Subjects Because the mean age of our control subjects was lower than the age of the CSCR subjects and the age of the chronic CSCR subjects was higher than the acute/recurrent subjects, we have analyzed whether serum LCN2 (NGAL) and NGAL/MMP9 levels were correlated with age in both the control and the CSCR cohorts. As shown in Tables 4 and 5, while levels of NGAL significantly correlates with NGAL/MMP9 levels, there was no correlation between age and either NGAL or NGAL/MMP9 in both the control and CSCR groups. Tables 6 and 7 show also that there was no correlation between age and both NGAL and NGAL/MMP9 serum levels within the acute/recurrent CSCR and within the chronic CSCR subjects, which exclude age as a confounding factor in our results.

Sex does not Influence LCN2 (NGAL) and NGAL/MMP9 Serum Levels Both in CSCR and in Control Subjects To ensure than sex ratio in the control and CSCR cohort could not interfere with our results, we have evaluated whether levels of LCN2 (NGAL) and NGAL/MMP9 were different in the male vs the female populations of CSCR and control subjects. Table 8 shows that levels of NGAL and NGAL/MMP9 did not correlate with sex in either populations.

ROC Curve Analysis

Figure 3:
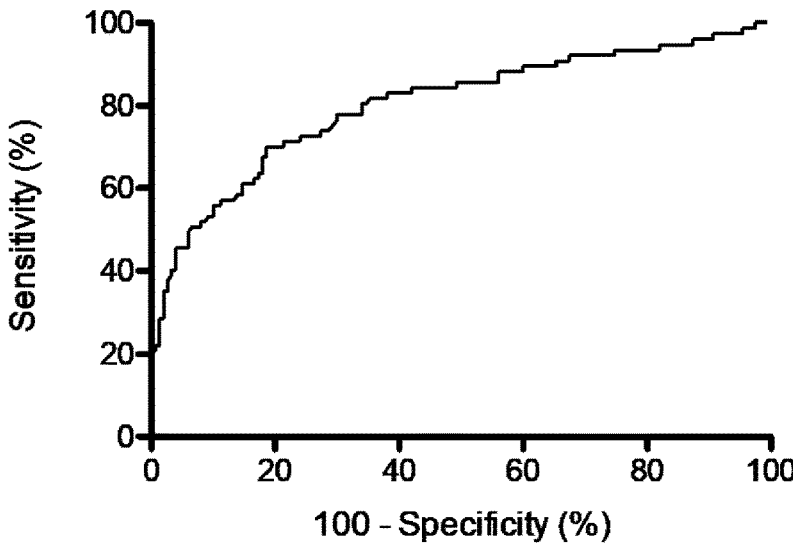

As shown in FIG. 2, ROC curve showed that for serum levels of NGAL, a cutoff value of 80 ng/mL allows to discriminate acute/recurrent CSCR (<80 ng/mL) from controls (>80 ng/mL) with 79.5% sensitivity and 74.8% specificity. For serum levels of the NGAL/MMP9 complex, a cutoff value of 40 ng/mL allows to discriminate acute/recurrent CSCR (<40 ng/mL) from controls (>40 ng/mL) with 72.7% sensitivity and 76.0% specificity (FIG. 3).

Risk of Relapse

We have shown, using transgenic rats that are KO for NGAL, that upon exposure to light, these rats have a significantly higher loss of photoreceptors, showing that lacking NGAL confers and increased sensitivity to light-induced oxidative stress (FIG. 6). These results demonstrate that low levels of NGAL are a risk factor for the severity of CSCR and are associated with a risk of relapse in a subject suffering from CSCR.

DISCUSSION

The results of this study show that patients with CSCR have lower LCN2 and LCN2/MM9 levels than control subjects. The fact that patients originate from 3 different cohorts reinforce this unexpected finding. The serum levels measured in the control subjects are in the range of other control populations (30 years old woman, 115±86 ng/ml)[32], (142 subjects, 72 male, 70 female, 56.8±11.57 years, 122.53±26.15 ng/ml)[33]. Similar to our observation, no significant correlations between LCN2 levels and age or sex have been found in other cohorts[34, 35]. Thus, although weakness of this study resides in the difference in age and sex ratio between control and CSCR subjects, these factors might not have interfered with our results.

In metabolic[21] and cardiac[36] diseases and, in acute kidney injury[23,24], elevated levels of LCN2 is considered as a disease biomarker. Plasma LCN2 has been identified as a early marker of diabetic retinopathy and increased LCN2 levels correlated with the severity of the retinopathy[30]. Increased LCN2 levels were also identified in plasma of patients with Stargardt disease, retinitis pigmentosa, and age-related macular degeneration as compared with healthy controls[10]. But surprisingly, in CSCR, LCN2 serum levels are decreased as compared to healthy controls. In addition, the NGAL/MMP9 complex is also decreased, suggesting an endogenous decreased production of LCN2 in CSCR patients. Moreover, patients without signs of epitheliopathy have lower levels of LCN2 and NGAL/MMP9 than patients with epitheliopathy although both forms have reduced levels as compared to controls. This finding shows a biological link between acute and chronic form of the disease that could be an underlying mechanism. As compared to other organs where LCN2 exerts rather pro-inflammatory effects, in the retina, LCN2 can have anti-inflammatory and anti-oxydant effects, particularly in case of pre-existing RPE pathology such as in Abca4−/−Rdh8−/− mice submitted to light[19]. Therefore, decreased levels of LCN2 could be deleterious for the RPE and contribute to CSCR pathogenesis leading to epitheliopathy observed in the chronic form of the disease. On the other hand, reduced NGAL/MMP9 means that lower MMP9 activity may protects the retina from leukocytes infiltration. Indeed, in the brain, MMP-9 from an immune cell source is required for the initial infiltration of leukocytes through the blood-brain barrier in experimental autoimmune encephalomyelitis[37] and leukocytes infiltration in the retina has been observed in the retina of patients with AMD as a consequence of the AKT2-NFkB-LCN2 axis[15].

Another interesting mechanistic finding is that LCN2 is one of the rare molecules, induced by NF-kB[12], that is up-regulated by glucocorticoids[38] and that exerts a negative feed-back on NF-kB activation and thus an anti-inflammatory effect in endotoxin-induced uveitis.[11] Similarly, LCN2 protects the brain against inflammation[16] and restored the blood-brain barrier disrupted after ischemic stress, enhancing directly the proper membrane distribution of ZO-1 and VE-Cadherin[39]. The paradoxical effects of glucocorticoids in CSCR patients, that instead of reducing retinal edema and RPE barrier breakdown are aggravating factor, could result from an improper regulation of lipocalin 2 by glucocorticoids.

Recently Parmar et al showed that LCN2 exerted strong dose-dependent protective effects against $H_2O_2$-induced cell death in hiPS-RPE through the up-regulation of the antioxidant enzymes heme oxygenase 1 (HMOX1) and superoxide dismutase 2 (SOD2). In addition, LCN2 protected hiPS-RPE cells from inflammatory-induced apoptosis and light stress enhanced the expression of the LCN2 receptor SLC22A17, sowing that LCN2, either produced by RPE cells or by immune cells may serve to protect the retina from inflammation and oxidative stress-induced degeneration[10]. Reduced serum LCN2 in CSCR patients could be involved in alteration of RPE barrier and excessive susceptibility to oxidative stress, which is supported by the recent observation that the disulfide/thiol ratio is significantly greater in CSCR patients relative to healthy control subjects[40]. On the other hand, reduction of NGAL/MMP9 complex might decrease MMP9 activity and therefore protects the blood retinal barrier, explaining that only the outer retinal barrier is disrupted in CSCR.

Whether LCN2 and NGAL/MMP9 serum levels reflect the ocular levels of LCN2 and how these levels vary upon corticoid simulation in CSCR patients as compared to healthy controls remain to be clarified.

In conclusion, decreased LCN2 in CSCR with and without epitheliopathy provides a biologic link between the two forms of the disease and a potential mechanistic link with the disease pathogenesis. It also suggests that CSCR might not be a condition limited to the eye but a more general deregulation of LCN2. To our knowledge, CSCR being the only ocular disease associated with decreased LCN2 level, it could be used as a biomarker of the disease, particularly when differential diagnosis with AMD is challenging.

Lipocalin 2 (NGAL) has been found significantly increased in the plasma of patients with AMD as compared to age-matched controls (*Plasma level of lipocalin 2 is increased in neovascular age-related macular degeneration patients, particularly those with macular fibrosis*. Chen M, et al. Immun Ageing. November 2020. PMID: 33292361). In dry AMD patients, plasma levels of lipocalin 2 have been shown to be increased as compared to controls (*Lipocalin 2 Plays an Important Role in Regulating Inflammation in Retinal Degeneration*. Parmar T, Parmar V M, Perusek L, Georges A, Takahashi M, Crabb J W, Maeda A. J Immunol. 2018 May 1; 200(9):3128-3141. doi: 10.4049/jimmunol.1701573). Lipocalin 2 levels is increased in the aqueous humor of patients with neovascular AMD as compared to patients operated for cataract without AMD (*The Intraocular Cytokine Profile and Therapeutic Response in Persistent Neovascular Age-Related Macular Degeneration*. Rezar-Dreindl S, Sacu S, Eibenberger K, Pollreisz A, Buhl W, Georgopoulos M, Krall C, Weigert G, Schmidt-Erfurth U. Invest Ophthalmol Vis Sci. 2016 Aug. 1; 57(10):4144-50). We have measured NGAL levels in the serum of patients with wet AMD as compared to controls and we found that there was a significant increase in NGAL serum levels (Controls: n=88, AMD:n=46) (FIG. 4). In addition, levels of NGAL were significantly higher in the serum of patients with wet AMD as compared to patients with CSCR (FIG. 5). This correlation could allow the use of NGAL levels for the differential diagnosis between CSCR and AMD.

Tables:

TABLE 1

| | | | | | | Chronic CSCR | |
| | | All CSCR | | Acute/recurrent CSCR | | (n = 90) | |
| | | (n = 168) | | (n = 78) | | | P value |
| | Controls (n = 153) | | P value (vs Controls) | | P value (vs Controls) | | P value (vs Controls) | (vs Acute/ recurrent CSCR) |
| Age (years) | 43.9 ± 12.8 | 50.1 ± 10.7 | 0.0002* | 44.1 ± 8.2 | 0.83* | 55.2 ± 9.9 | <0.0001* | <0.0001* |
| Male/ female (No.) | 112/41 | 141/27 | 0.021† | 69/9 | 0.007† | 72/18 | 0.28† | 0.15† |

Demographic characteristics of 168 patients with CSCR and 153 controls

*= Mann-Whitney test

†= Fisher's exact test

TABLE 2

Serum levels of lipocalin (NGAL) and the lipocalin/MMP9 (NGAL/MMP9)
complex in 168 patients with CSCR and 153 controls

| | Controls (n = 153) | All CSCR (n = 168) | | Acute/recurrent CSCR (n = 78) | | Chronic CSCR (n = 90) | | |
|---|---|---|---|---|---|---|---|---|
| | | | P value* (vs Controls) | | P value* (vs Controls) | | P value* (vs Controls) | P value* (vs Acute/ recurrent CSCR) |
| NGAL (ng/ml) | 108.8 ± 46.8 | 80.4 ± 46.4 | <0.0001 | 71.3 ± 32.1 | <0.0001 | 88.3 ± 55.0 | <0.0001 | 0.003 |
| NGAL/MMP9 (ng/ml) | 77.6 ± 47.8 | 44.5 ± 39.6 | <0.0001 | 37.6 ± 37.9 | <0.0001 | 50.5 ± 40.3 | <0.0001 | 0.002 |

Quantitative data are reported as mean ± standard deviation
*Mann-Whitney test

TABLE 3

Serum levels of lipocalin (NGAL) and the lipocalin/MMP9 complex
(NGAL/MMP9) in 141 male patients with CSCR and 112 male controls

| | Control males (n = 112) | All CSCR males (n = 141) | | Acute/recurrent CSCR males (n = 69) | | Chronic CSCR males (n = 72) | | |
|---|---|---|---|---|---|---|---|---|
| | | | P value* (vs Controls) | | P value* (vs Controls) | | P value* (vs Controls) | P value* (vs Acute/ recurrent CSCR) |
| NGAL (ng/ml) | 101.5 ± 41.7 | 80.7 ± 47.7 | <0.0001 | 71.9 ± 33.1 | <0.0001 | 89.1 ± 57.5 | <0.0001 | 0.004 |
| NGAL/MMP9 (ng/ml) | 72.2 ± 42.7 | 43.1 ± 137.8 | <0.0001 | 36.8 ± 38.5 | <0.0001 | 49.1 ± 36.4 | <0.0001 | 0.001 |

Quantitative data are reported as mean ± standard deviation
*Mann-Whitney test

TABLE 4

Correlation between age and serum levels of
lipocalin (NGAL) and the lipocalin/MMP9 complex
(NGAL/MMP9) among 153 control patients

| P value (Spearman r*) | Age (years) | NGAL (ng/mL) |
|---|---|---|
| NGAL (ng/mL) | 0.99 (r = −0.001) | |
| NGAL/MMP9 (ng/mL) | 0.28 (r = −0.09) | <0.0001 (r = 0.72) |

*Correlations were assessed using the Spearman correlation coefficient

TABLE 6

Correlation between age and serum levels of lipocalin
(NGAL) and the lipocalin/MMP9 complex (NGAL/MMP9)
among 78 patients with acute/recurrent CSCR

| P value (Spearman r*) | Age (years) | NGAL (ng/mL) |
|---|---|---|
| NGAL (ng/mL) | 0.43 (r = 0.09) | |
| NGAL/MMP9 (ng/mL) | 0.008 (r = 0.30) | <0.0001 (r = 0.48) |

*Correlations were assessed using the Spearman correlation coefficient

TABLE 5

Correlation between age and serum levels of
lipocalin (NGAL) and the lipocalin/MMP9 complex
(NGAL/MMP9) among 168 patients with CSCR

| P value (Spearman r*) | Age (years) | NGAL (ng/mL) |
|---|---|---|
| NGAL (ng/mL) | 0.058 (r = 0.15) | |
| NGAL/MMP9 (ng/mL) | 0.15 (r = 0.11) | <0.0001 (r = 0.62) |

*Correlations were assessed using the Spearman correlation coefficient

TABLE 7

Correlation between age and serum levels of lipocalin
(NGAL) and the lipocalin/MMP9 complex (NGAL/MMP9)
among 90 patients with chronic CSCR

| P value (Spearman r*) | Age (years) | NGAL (ng/mL) |
|---|---|---|
| NGAL (ng/mL) | 0.90 (r = −0.09) | |
| NGAL/MMP9 (ng/mL) | 0.19 (r = −0.31) | <0.0001 (r = 0.64) |

*Correlations were assessed using the Spearman correlation coefficient

TABLE 8

| Comparison of lipocalin/MMP9 complex (NGAL/MMP9) serum levels in male and female subjects | | | |
| --- | --- | --- | --- |
| NGAL/MMP9 (ng/mL) | Male | Female | P value* |
| Acute/recurrent CSCR | 36.8 ± 38.5 | 43.9 ± 34.8 | 0.33 |
| Chronic CSCR | 49.1 ± 36.4 | 56.2 ± 53.6 | 0.89 |
| Controls | 72.2 ± 42.7 | 92.3 ± 57.6 | 0.077 |

*Mann-Whitney test

REFERENCES

Throughout this application, various references describe the state of the art to which this invention pertains. The disclosures of these references are hereby incorporated by reference into the present disclosure.

1. Singh, S. R. et al. Discrepancy in current central serous chorioretinopathy classification. Br. J. Ophthalmol. (2018) doi:10.1136/bjophthalmol-2018-312435.
2. Daruich, A. et al. Central serous chorioretinopathy: Recent findings and new physiopathology hypothesis. Prog. Retin. Eye Res. 48, 82-118 (2015).
3. Liu, B., Deng, T. & Zhang, J. RISK FACTORS FOR CENTRAL SEROUS CHORIORETINOPATHY: A Systematic Review and Meta-Analysis. Retina Phila. Pa 36, 9-19 (2016).
4. Schellevis, R. L. et al. Role of the Complement System in Chronic Central Serous Chorioretinopathy: A Genome-Wide Association Study. JAMA Ophthalmol. 136, 1128-1136 (2018).
5. van Dijk, E. H. C. et al. Association of a Haplotype in the NR3C2 Gene, Encoding the Mineralocorticoid Receptor, With Chronic Central Serous Chorioretinopathy. JAMA Ophthalmol. 135, 446-451 (2017).
6. Malle, E. M. et al. Role of the tissue-type plasminogen activator −7351C>T and plasminogen activator inhibitor 1 4G/5G gene polymorphisms in central serous chorioretinopathy. Ophthalmic Genet. 39, 714-716 (2018).
7. Hosoda, Y. et al. CFH and VIPR2 as susceptibility loci in choroidal thickness and pachychoroid disease central serous chorioretinopathy. Proc. Natl. Acad. Sci. U.S.A. 115, 6261-6266 (2018).
8. Xiao, X., Yeoh, B. S. & Vijay-Kumar, M. Lipocalin 2: An Emerging Player in Iron Homeostasis and Inflammation. Annu. Rev. Nutr. 37, 103-130 (2017).
9. Nairz, M., Haschka, D., Demetz, E. & Weiss, G. Iron at the interface of immunity and infection. Front. Pharmacol. 5, 152 (2014).
10. Parmar, T. et al. Lipocalin 2 Plays an Important Role in Regulating Inflammation in Retinal Degeneration. J. Immunol. Baltim. Md 1950 200, 3128-3141 (2018).
11. Tang, W. et al. Lipocalin 2 Suppresses Ocular Inflammation by Inhibiting the Activation of NF-κβ Pathway in Endotoxin-Induced Uveitis. Cell. Physiol. Biochem. Int. J. Exp. Cell. Physiol. Biochem. Pharmacol. 46, 375-388 (2018).
12. Iannetti, A. et al. The neutrophil gelatinase-associated lipocalin (NGAL), a NF-kappaB-regulated gene, is a survival factor for thyroid neoplastic cells. Proc. Natl. Acad. Sci. U.S.A. 105, 14058-14063 (2008).
13. Xavier, A. M., Anunciato, A. K. O., Rosenstock, T. R. & Glezer, I. Gene Expression Control by Glucocorticoid Receptors during Innate Immune Responses. Front. Endocrinol. 7, 31 (2016).
14. Moschen, A. R., Adolph, T. E., Gerner, R. R., Wieser, V. & Tilg, H. Lipocalin-2: A Master Mediator of Intestinal and Metabolic Inflammation. Trends Endocrinol. Metab. TEM 28, 388-397 (2017).
15. Ghosh, S. et al. Neutrophils homing into the retina trigger pathology in early age-related macular degeneration. Commun. Biol. 2, 348 (2019).
16. Kang, S. S. et al. Lipocalin-2 protects the brain during inflammatory conditions. Mol. Psychiatry 23, 344-350 (2018).
17. Yan, L., Borregaard, N., Kjeldsen, L. & Moses, M. A. The high molecular weight urinary matrix metalloproteinase (MMP) activity is a complex of gelatinase B/MMP-9 and neutrophil gelatinase-associated lipocalin (NGAL). Modulation of MMP-9 activity by NGAL. J. Biol. Chem. 276, 37258-37265 (2001).
18. Amersfoort, J. et al. Lipocalin-2 contributes to experimental atherosclerosis in a stage-dependent manner. Atherosclerosis 275, 214-224 (2018).
19. Parmar, T. et al. Acute Stress Responses Are Early Molecular Events of Retinal Degeneration in Abca4−/−Rdh8−/− Mice After Light Exposure. Invest. Ophthalmol. Vis. Sci. 57, 3257-3267 (2016).
20. Tang, W. et al. Light-Induced Lipocalin 2 Facilitates Cellular Apoptosis by Positively Regulating Reactive Oxygen Species/Bim Signaling in Retinal Degeneration. Invest. Ophthalmol. Vis. Sci. 59, 6014-6025 (2018).
21. Abella, V. et al. The potential of lipocalin-2/NGAL as biomarker for inflammatory and metabolic diseases. Biomark. Biochem. Indic. Expo. Response Susceptibility Chem. 20, 565-571 (2015).
22. Sun, Y. et al. Aldosterone-induced inflammation in the rat heart: role of oxidative stress. Am. J. Pathol. 161, 1773-1781 (2002).
23. Antonucci, E. et al. Neutrophil gelatinase-associated lipocalin (NGAL): a promising biomarker for the early diagnosis of acute kidney injury (AKI). Acta Bio-Medica Atenei Parm.
24. Haase, M. et al. Accuracy of neutrophil gelatinase-associated lipocalin (NGAL) in diagnosis and prognosis in acute kidney injury: a systematic review and meta-analysis. Am. J. Kidney Dis. Off. J. Natl. Kidney Found. 54, 1012-1024 (2009).
25. Haase-Fielitz, A., Haase, M. & Devaraj an, P. Neutrophil gelatinase-associated lipocalin as a biomarker of acute kidney injury: a critical evaluation of current status. Ann. Clin. Biochem. 51, 335-351 (2014).
26. Buonafine, M., Martinez-Martinez, E. & Jaisser, F. More than a simple biomarker: the role of NGAL in cardiovascular and renal diseases. Clin. Sci. Lond. Engl. 1979 132, 909-923 (2018).
27. Sivalingam, Z. et al. Neutrophil gelatinase-associated lipocalin as a risk marker in cardiovascular disease. Clin. Chem. Lab. Med. 56, 5-18 (2017).
28. Horckmans, M. et al. Neutrophils orchestrate post-myocardial infarction healing by polarizing macrophages towards a reparative phenotype. Eur. Heart J. 38, 187-197 (2017).
29. Koban, Y., Sahin, S., Boy, F. & Kara, F. Elevated lipocalin-2 level in aqueous humor of patients with central retinal vein occlusion. Int. Ophthalmol. 39, 981-986 (2019).
30. Chung, J. O., Park, S. Y., Cho, D. H., Chung, D. J. & Chung, M. Y. Plasma neutrophil gelatinase-associated lipocalin levels are positively associated with diabetic retinopathy in patients with Type 2 diabetes. Diabet. Med. J. Br. Diabet. Assoc. 33, 1649-1654 (2016).

31. Rezar-Dreindl, S. et al. The Intraocular Cytokine Profile and Therapeutic Response in Persistent Neovascular Age-Related Macular Degeneration. Invest. Ophthalmol. Vis. Sci. 57, 4144-4150 (2016).

32. Cymbaluk-Ploska, A. et al. The role of lipocalin-2 serum levels in the diagnostics of endometrial cancer. Cancer Biomark. Sect. Dis. Markers 24, 315-324 (2019).

33. Wang, W. et al. Elevated serum lipocalin 2 levels are associated with indexes of both glucose and bone metabolism in type 2 diabetes mellitus. Endokrynol. Pol. 69, 276-282 (2018).

34. Stejskal, D. et al. Lipocalin-2: development, analytical characterization, and clinical testing of a new ELISA. Horm. Metab. Res. Horm. Stoffwechselforschung Horm. Metab. 40, 381-385 (2008).

35. Meier, E. M. et al. Circulating lipocalin 2 is neither related to liver steatosis in patients with non-alcoholic fatty liver disease nor to residual liver function in cirrhosis. Cytokine 85, 45-50 (2016).

36. Martinez-Martinez, E. et al. Aldosterone Target NGAL (Neutrophil Gelatinase-Associated Lipocalin) Is Involved in Cardiac Remodeling After Myocardial Infarction Through NFκB Pathway. Hypertens. Dallas Tex 1979 70, 1148-1156 (2017).

37. Gerwien, H. et al. Imaging matrix metalloproteinase activity in multiple sclerosis as a specific marker of leukocyte penetration of the blood-brain barrier. Sci. Transl. Med. 8, 364ra152 (2016).

38. Owen, H. C., Roberts, S. J., Ahmed, S. F. & Farquharson, C. Dexamethasone-induced expression of the glucocorticoid response gene lipocalin 2 in chondrocytes. Am. J. Physiol. Endocrinol. Metab. 294, E1023-1034 (2008).

39. Du, Y., Li, W., Lin, L., Lo, E. H. & Xing, C. Effects of lipocalin-2 on brain endothelial adhesion and permeability. PloS One 14, e0218965 (2019).

40. Turkoglu, E. B. et al. Thiol/Disulfide Homeostasis in Patients with Central Serous Chorioretinopathy. Curr. Eye Res. 41, 1489-1491 (2016).

The invention claimed is:

1. A method of determining that a subject has or is at risk of having a central serous chorioretinopathy (CSCR) and treating the subject, comprising i) measuring a level of neutrophil gelatinase-associated lipocalin (NGAL) in a sample selected from the group consisting of blood, plasma and serum obtained from the subject, wherein the subject is a human;

ii) determining the level of NGAL is lower than a predetermined reference value, wherein a difference between the level of NGAL and the predetermined reference value is statistically significant with a p value of 0.03 or less, wherein the predetermined reference value is the level of NGAL determined in samples obtained from a population of healthy individuals, and wherein the difference indicates that the subject has or is at risk of having CSCR; and iii) administering a treatment for CSCR to the subject, wherein the treatment is a drug or therapy selected from the group consisting of anti-VEGF agents, carbonic anhydrase inhibitors, mineralocorticoid (MR) antagonists, laser photocoagulation, diode micropulse laser, verteporfin photodynamic therapy (PDT) and transpupillary thermotherapy.

2. The method of claim 1 wherein the sample is a serum sample.

3. A method of predicting the risk of relapse of CSCR in a subject previously treated for CSCR and treating the subject, comprising measuring the level of neutrophil gelatinase-associated lipocalin (NGAL) in a blood sample obtained from the subject, wherein the subject is a human;

determining that the level of NGAL is lower than a predetermined reference value for NGAL measured in blood samples from a population of healthy individuals, wherein the difference between the level of NGAL is statistically significant with a p value of 0.03 or less, indicating that the subject has or is at risk of having a relapse of CSCR; and administering a treatment for CSCR to the subject determined to have the lower level of NGAL, wherein the treatment is a drug or therapy selected from the group consisting of anti-VEGF agents, carbonic anhydrase inhibitors, mineralocorticoid (MR) antagonists, laser photocoagulation, diode micropulse laser, verteporfin photodynamic therapy (PDT) and transpupillary thermotherapy.

4. The method of claim 1 wherein the treatment is an MR antagonist that is spironolactone or eplerenone.

5. The method of claim 3 wherein the sample is a serum sample.

6. The method of claim 1, wherein the statistically significantly lower level for the subject is at least 18% lower.

7. The method of claim 3, wherein the statistically significantly lower level for the subject is at least 18% lower.

* * * * *